United States Patent [19]

Malpass et al.

[11] Patent Number: 4,670,571

[45] Date of Patent: Jun. 2, 1987

[54] METHOD FOR RECOVERY OF ALKYLALUMINUM HALIDES

[75] Inventors: Dennis B. Malpass, LasPorte; Loyd W. Fannin, Dickinson, both of Tex.

[73] Assignee: Texas Alkyls, Inc., Deer Park, Tex.

[21] Appl. No.: 787,208

[22] Filed: Oct. 15, 1985

[51] Int. Cl.$^4$ .............................. C07F 3/06; C07F 5/06
[52] U.S. Cl. ..................................... 556/129; 556/186
[58] Field of Search ............................... 556/186, 129

[56] References Cited

U.S. PATENT DOCUMENTS

| | | | |
|---|---|---|---|
| 2,996,529 | 8/1961 | Bos | 556/186 |
| 3,061,647 | 10/1962 | Jenkner | 556/186 X |
| 3,072,697 | 1/1963 | Jenkner | 556/186 X |
| 3,074,986 | 1/1963 | Köster et al. | 556/186 |
| 3,080,409 | 3/1963 | Cook et al. | 556/186 X |
| 3,124,604 | 3/1964 | Hüther | 556/186 X |
| 3,475,475 | 10/1969 | Eidt | 556/186 X |
| 3,946,058 | 3/1976 | Malpass et al. | 556/186 |
| 4,092,342 | 5/1978 | Mueller | 556/186 |
| 4,116,992 | 9/1978 | Eidt | 556/186 |

*Primary Examiner*—Helen M. S. Sneed
*Attorney, Agent, or Firm*—Joel G. Ackerman

[57] ABSTRACT

Dialkylaluminum chloride produced as a co-product in the reaction of a trialkylaluminum with zinc chloride or metallic zinc and an alkyl halide, to produce a dialkylzinc, is purified from contaminants containing zinc by contacting it with an alkylaluminum sesquihalide, followed by distillation.

7 Claims, No Drawings

METHOD FOR RECOVERY OF ALKYLALUMINUM HALIDES

BACKGROUND AND PRIOR ART

This invention relates to a method for the recovery of alkylaluminum halides, particularly dialkylaluminum chlorides, from mixtures also containing zinc alkyls.

Several processes are known in the art for producing zinc alkyls, such as diethylzinc, from trialkylaluminum compounds and zinc-containing materials. One such process, described in U.S. Pat. No. 3,124,604, involves the reaction of an aluminum trialkyl with zinc chloride, producing the dialkylzinc together with co-product dialkylaluminum chloride. In another method, described in U.S. Pat. No. 3,080,409, a trialkylaluminum compound is reacted with zinc chloride in the presence of an organoaluminum halide. Yet a third process, described in U.S. Pat. No. 3,475,475, involves the reaction of a trialkylaluminum compound with zinc and an alkyl or other organic halide.

The desired dialkylzinc product is relatively readily recovered by vacuum distillation (e.g., 47° C. at 50 torr) from the product mixture. However, the reaction co-product, dialkylaluminum halide, is contaminated with zinc-containing materials. These include higher boiling zinc alkyls such as (in the production of diethyl zinc) di-n-butyl zinc and ethyl-n-butyl zinc. These may be formed from higher boiling impurities in the trialkylaluminum or alkyl halide reactant. For instance, triethylaluminum used as a reactant may contain impurities having n-butyl groups which also react with the zinc chloride or metallic zinc to produce dialkylzincs containing n-butyl groups.

The usual method by which the desired dialkylaluminum halide co-product (for instance, diethylaluminum chloride) is to be recovered is by distillation from the residue remaining after distillation of the dialkylzinc. However, it has been found that the higher boiling zinc alkyls tend to co-distill together with the dialkylaluminum halide so that this product, after recovery, is contaminated with substantial amounts of higher boiling zinc alkyls.

Several methods have been proposed to recover the dialkylaluminum halide co-product, with relatively little zinc content. For instance, U.S. Pat. No. 3,946,058 teaches to heat the mixture strongly before such distillation in order to pyrolyze the zinc-containing compounds. However, this heating process must be carried out for a fairly long period of time (4–10 hours) at a temperature range of about 150°–240° C., which encompasses the decomposition temperature of dialkylaluminum chlorides. Additionally, zinc is formed as a product of the pyrolysis, and the zinc particles tend to clump together, producing clogging.

Another process which has been proposed for recovery of dialkylaluminum halides with a lower zinc content is described in U.S. Pat. No. 4,092,342. In this process, a dialkylaluminum chloride is treated, prior to distillation, with solid aluminum chloride. The amount of aluminum chloride utilized depends on whether or not the dialkylaluminum chloride-containing mixture also includes unreacted trialkylaluminum. This process is said to produce a diethylaluminum chloride mixture containing, in some cases less than 10 ppm zinc. However, this process still requires a heating step (at about 150° C.) prior to the addition of the aluminum chloride, and also involves the use of solid aluminum chloride, which may require additional handling.

SUMMARY OF THE INVENTION

This invention comprises an improvement in a process for production of dialkylzinc compounds by reaction of a trialkylaluminum compound with either zinc chloride or metallic zinc and an alkyl halide, in which a dialkylaluminum halide is produced as a co-product, the dialkylzinc is removed from the reaction products by distillation, and the dialkylaluminum halide is thereafter removed from the reaction products by distillation, which improvement comprises contacting the dialkylaluminum halide, prior to removal of it by distillation, with an alkylaluminum sesquihalide.

DETAILED DESCRIPTION OF THE INVENTION

The material which is treated by the process of this invention consists mainly of a dialkylaluminum halide. The nature of the alkyl and halide components will depend on the process by which the primary product, dialkylzinc, was prepared (referred to as the "dialkylzinc process"). In the description of this invention, reference will be made in general to a process for production of diethyl zinc by reaction of triethylaluminum with either zinc chloride or metallic zinc and ethyl chloride. However, other dialkylzinc compounds may be produced by this process, by the reaction of trialkylaluminum compounds other than triethylaluminum and the use of alkyl halides, including iodides and bromides, other than ethyl chloride. In a preferred embodiment of this process, therefore, the dialkylaluminum halide which is to be treated for removal of zinc-containing contaminants is a lower alkylaluminum halide, preferably one containing from 1 to 4 carbon atoms in the alkyl group. More preferably this compound is a lower alkylaluminum chloride, and most preferably diethylaluminum chloride.

Also, for purposes of convenience, the improvement which comprises this invention will be referred to specifically in terms of treatment with ethyl aluminum sesquichloride (EASC), but the process may be carried out using other alkylaluminum sesquihalides in which the alkyl group or groups contains from 1 to 4 carbon atoms.

In the dialkylzinc process, a dialkylzinc compound such as diethylzinc is produced by reaction of the corresponding trialkylaluminum compound (in this case triethylaluminum) with either zinc chloride or metallic zinc and the corresponding alkyl halide (in this case ethyl chloride).

The reaction of triethylaluminum with zinc chloride is described in U.S. Pat. No. 3,124,604 and is carried out without a catalyst. See, for instance, Example I of this U.S. patent.

The production of diethyl zinc by reaction of metallic zinc (i.e., zinc dust), triethylaluminum and ethyl chloride is described in U.S. Pat. No. 3,,475,475. This process may be enhanced by the inclusion of elemental iodine as a catalyst.

Whichever process is used, the reaction product comprises primarily two components: the desired zinc alkyl, i.e., diethylzinc and a dialkylaluminum halide, i.e., diethylaluminum chloride. In the reaction between zinc chloride and triethylaluminum, the diethylaluminum chloride is produced in twice the molar amount of diethylzinc, because of reaction stoichiometry.

As is known in the prior art, the diethylzinc product is readily removed from the total reaction products by appropriate distillation, for instance, vacuum distillation. The major component of the remaining product is thus diethylaluminum chloride, which will contain various amounts and types of zinc impurities, such as unreacted zinc chloride, minor amounts of undistilled diethylzinc, and volatile zinc alkyls having higher boiling points than that of diethylzinc. Such zinc alkyls would include, for instance, di-n-butylzinc and n-butylethylzinc, which are believed to be produced in the dialkylzinc process by reaction of zinc chloride with n-butyl-containing contaminants in either the triethylaluminum or ethyl chloride. When, as conventionally, the co-product diethylaluminum chloride is recovered by distillation, these volatile zinc alkyl impurities generally tend to distill off with the diethylaluminum chloride and contaminate this product.

According to this invention, the addition of ethylaluminum sesquichloride (EASC) or another lower alkyl-aluminum sesquihalide to the diethylaluminum chloride product after distillation of diethylzinc has been completed but before distillation of diethylaluminum chloride is carried out, enables the recovery of a mixture of ethylaluminum chlorides containing relatively low amounts of zinc contaminants. The mixture thus recovered (which includes both diethylaluminum chloride and EASC) can be converted to diethylaluminum chloride by blending with an appropriate quantity of triethylaluminum.

The amount of EASC employed is from about 0.10:1 to about 1.50:1 by weight, with respect to the weight of diethylaluminum chloride. Preferably, the weight ratio is from about 0.25:1 to about 0.45:1. The chlorine/aluminum mole ratio in the EASC/diethylaluminum chloride mixture would range from about 1.05–1.30, preferably about 1.10–1.15.

The distillation and recovery of diethylaluminum chloride from the contaminated material is carried out according to known techniques. The material, after distillation and recovery, according to this invention, contains generally less than about 600 ppm zinc, and in most cases substantially less than that amount.

ethylaluminum chloride and 1 molar equivalent of diethylzinc.

Diethylzinc was distilled off from the reaction product by vacuum distillation at about 48° C. under 50±2 torr pressure with the pot temperature not exceeding 135° C.

Subsequently, diethylaluminum chloride was removed from the remaining materials by vacuum distillation at about 88° C. under a pressure of 10±2 torr. Generally, multiple fractions of diethylaluminum chloride were collected to determine if zinc contamination could be minimized by removing a fore-cut or if the content of butyl components in the product could be minimized by taking less product overhead. In the table which follows, all fractions of diethylaluminum chloride are combined and the total quantity reported.

The diethylaluminum chloride distilled was hydrolyzed and analyzed for zinc by complexiometric titration with EDTA (ethylene diaminetetraacetic acid) using zinc sulfate for back titration. Several of the dialkylaluminum chloride distillates showing nil zinc by this analysis were also analyzed by atomic absorption.

The following table contains results of six experiments. Three experiments were performed without the addition of ethylaluminum sesquichloride to the diethylaluminum chloride-containing mixture before the latter was removed by distillation. The last three, experiments 4–6, were performed according to the invention. In these experiments, the indicated amount of ethylaluminum sesquichloride was added to the still pot after distillation of diethylzinc but before distillation of diethylaluminum chloride. The ethylaluminum sesquichloride, which is a liquid, was added with no heating step or other process change. In this table are given the quantities of overall reaction product (of the reaction between zinc chloride and triethylaluminum), the amount of diethylzinc collected after distillation of that substance, the amount of diethylaluminum chloride or mixture of diethylaluminum chloride with EASC collected in the second distillation step, and the weight percent of zinc found in the dialkylaluminum chloride product collected, in terms of elemental zinc.

TABLE

| Expt No. | Reaction product, grams | $(C_2H_5)_2Zn$ collected, grams | Total alkyl aluminum chlorides collected, grams | EASC added grams | Total alkyl aluminum chlorides Cl/Al mole ratio | Zn content of Total alkyl aluminum chlorides wt. % | Soluble Zn content of still pot residue wt. % |
|---|---|---|---|---|---|---|---|
| 1 | 97.5 | 26.8 | 64.4 | — | 0.90 | 1.86 | * |
| 2 | 87.2 | 26.6 | 51.4 | — | 1.01 | 0.88 | 1.10 |
| 3 | 127.7 | 41.1 | 78.5 | — | 0.99 | 0.94 | 0.61 |
| 4 | 123.5 | 39.8 | 150.9 | 77.0 | 1.28 | nil | 5.07 |
| 5 | 121.1 | 38.0 | 110.1 | 43.3 | 1.21 | nil | 4.95 |
| 6 | 127.1 | 39.5 | 91.8 | 19.8 | 1.11 | nil | 3.6 |

* = No analysis made.

The conduct of the process according to this invention is illustrated in greater detail in the examples which follow.

EXAMPLES

General Procedure

Preparations of diethylzinc were carried out by the slow addition of 1 molar equivalent of anhydrous zinc chloride powder to 2 molar equivalents of triethylaluminum, followed by heating to about 75° C. for one hour. A quantity of reaction product was obtained, which contained essentially 2 molar equivalents of di- As can be seen from the foregoing table, substantial amounts of zinc were found in the diethylaluminum chloride product in Examples 1–3, conducted without the addition of ethylaluminum sesquichloride. When EASC was added, as shown in Experiments 4–6, analysis of zinc content in the alkylaluminum chloride product showed a result of "nil" which, as mentioned above, was determined in some cases by atomic absorption to be between 45 and 600 ppm. Comparison of the soluble zinc content of the still pot residue after distillation of mixed alkylaluminum chlorides shows that, as compared to Experiments 1–3 (with no EASC added) the zinc essentially remained in the still pot and was not carried over with the distilled product.

What is claimed is:

1. In a process for the production of dialkylzinc compounds by reaction of a trialkylaluminum compound with either zinc chloride or metallic zinc and an alkyl halide, in which a dialkylaluminum halide is produced as a co-product, the dialkylzinc is removed from the reaction products by distillation, and the dialkylaluminum halide is thereafter removed from the reaction products by distillation, the improvement comprising contacting the dialkylaluminum halide, prior to removal of it by distillation, with an alkylaluminum sesquihalide.

2. A process according to claim 1 in which the alkylaluminum sesquihalide has from 1 to 4 carbon atoms in the alkyl group or groups.

3. A process according to claim 1 in which the alkylaluminum sesquihalide is a sesquichloride.

4. A process according to claim 1 in which the alkylaluminum sesquihalide is ethylaluminum sesquichloride.

5. A process according to claim 1 in which the amount of alkylaluminum sesquihalide added is from about 0.10:1 to about 1.50:1 by weight with respect to the dialkylaluminum halide.

6. A process according to claim 1 in which the dialkylzinc compound is produced by the reaction of a trialkylaluminum compound with zinc chloride.

7. A process according to claim 1 in which the trialkylaluminum is triethylaluminum, the dialkylzinc compound is diethylzinc, the dialkylaluminum chloride is diethylaluminum chloride, and the alkylaluminum sesquihalide is ethylaluminum sesquichloride.

* * * * *